US010842780B2

(12) United States Patent
Takaishi et al.

(10) Patent No.: US 10,842,780 B2
(45) Date of Patent: Nov. 24, 2020

(54) PHARMACEUTICAL COMPOSITION FOR MODIFIED RELEASE

(71) Applicant: ASTELLAS PHARMA INC., Tokyo (JP)

(72) Inventors: Yuuki Takaishi, Tokyo (JP); Yutaka Takahashi, Tokyo (JP); Takashi Nishizato, Tokyo (JP); Daisuke Murayama, Tokyo (JP); Emiko Murayama, Tokyo (JP); Soichiro Nakamura, Tokyo (JP); Kazuhiro Sako, Tokyo (JP)

(73) Assignee: ASTELLAS PHARMA INC., Tokyo (JP)

( * ) Notice: Subject to any disclaimer, the term of this patent is extended or adjusted under 35 U.S.C. 154(b) by 0 days.

(21) Appl. No.: 15/432,854

(22) Filed: Feb. 14, 2017

(65) Prior Publication Data

US 2017/0231965 A1    Aug. 17, 2017

Related U.S. Application Data

(63) Continuation of application No. 12/568,313, filed on Sep. 28, 2009, now abandoned.

(60) Provisional application No. 61/101,338, filed on Sep. 30, 2008.

(51) Int. Cl.
*A61K 31/426* (2006.01)
*A61K 9/20* (2006.01)
*A61K 9/28* (2006.01)

(52) U.S. Cl.
CPC .......... *A61K 31/426* (2013.01); *A61K 9/2009* (2013.01); *A61K 9/2013* (2013.01); *A61K 9/2031* (2013.01); *A61K 9/2054* (2013.01); *A61K 9/2095* (2013.01); *A61K 9/2853* (2013.01); *A61K 9/2866* (2013.01)

(58) Field of Classification Search
None
See application file for complete search history.

(56) References Cited

U.S. PATENT DOCUMENTS

| | | | |
|---|---|---|---|
| 4,929,629 A | 5/1990 | Jeffery | |
| 5,681,582 A | 10/1997 | Gilis et al. | |
| 6,204,285 B1 | 3/2001 | Fabiano et al. | |
| 6,346,532 B1 | 2/2002 | Maruyama et al. | |
| 6,368,628 B1 | 4/2002 | Seth | |
| 6,436,441 B1 | 8/2002 | Sako et al. | |
| 6,699,503 B1 | 3/2004 | Sako et al. | |
| 7,442,387 B2 | 10/2008 | Sugihara et al. | |
| 8,877,214 B2 | 11/2014 | Takaishi et al. | |
| 2001/0006982 A1 | 7/2001 | Cruz et al. | |
| 2003/0198619 A1 | 10/2003 | Dong et al. | |
| 2003/0203024 A1 | 10/2003 | Sako et al. | |
| 2004/0033263 A1 | 2/2004 | Seroff et al. | |
| 2004/0213845 A1 | 10/2004 | Sugihara et al. | |
| 2005/0100602 A1 | 5/2005 | Sako et al. | |
| 2005/0100603 A1 | 5/2005 | Sako et al. | |
| 2005/0261328 A1 | 11/2005 | Wienrich | |
| 2005/0287185 A1 | 12/2005 | Wong et al. | |
| 2006/0099257 A1 | 5/2006 | Langridge et al. | |
| 2006/0115540 A1 | 6/2006 | Takasu et al. | |
| 2008/0275076 A1 | 11/2008 | Holm et al. | |
| 2009/0011018 A1 | 1/2009 | Kondo et al. | |
| 2009/0093529 A1 | 4/2009 | Takasu et al. | |
| 2010/0144807 A1 | 6/2010 | Takaishi et al. | |

FOREIGN PATENT DOCUMENTS

| | | |
|---|---|---|
| AU | 199889288 B2 | 5/1999 |
| CA | 2263659 A1 | 2/1998 |
| CA | 2315235 A1 | 6/1999 |
| CA | 2328348 A1 | 10/1999 |
| CA | 2336853 A1 | 1/2000 |
| CA | 2507266 A1 | 6/2004 |
| CA | 2144077 C | 5/2005 |
| CA | 2490299 C | 8/2008 |
| CA | 2305802 C | 11/2008 |
| CA | 2387705 C | 6/2009 |
| EP | 1 205 190 A1 | 5/2002 |
| EP | 1 440 969 A1 | 7/2004 |
| EP | 1 559 427 A1 | 8/2005 |
| EP | 1 974 725 A1 | 10/2008 |
| EP | 2 345 410 A1 | 7/2011 |
| EP | 2 554 168 B1 | 1/2018 |
| GB | 2356197 A | 5/2001 |
| JP | S40-2053 | 2/1965 |

(Continued)

OTHER PUBLICATIONS

Daewoong Pharmaceutical Co., Ltd.; Petitioner's Brief; 2017 Dang 473 Patent Invalidation Action; Feb. 21, 2017.
Australian Patent Application No. 2009300752, Examination Report, dated Dec. 14, 2012, 11 pages.
Canadian Patent Application No. 2,740,342, Office Action, dated Jun. 3, 2013, 3 pages.
Canadian Patent Application No. 2,740,342, Second Office Action, dated Feb. 14, 2014, 2 pages.
Chinese Patent Application No. 200980138691.9, Decision on Rejection, dated Feb. 14, 2014, 5 pages.

(Continued)

*Primary Examiner* — Jeffrey S Lundgren
*Assistant Examiner* — Michael J Schmitt
(74) *Attorney, Agent, or Firm* — Venable LLP

(57) ABSTRACT

A pharmaceutical composition for modified release, comprising (1) (R)-2-(2-aminothiazol-4-yl)-4'-[2-[(2-hydroxy-2-phenylethyl)amino]ethyl]acetic acid anilide, or a pharmaceutically acceptable salt thereof, (2) at least one additive which ensures penetration of water into the pharmaceutical composition and which has a solubility such that the volume of water required for dissolving 1 g of the additive is 10 mL or less, and (3) a hydrogel-forming polymer having an average molecular weight of approximately 100,000 or more, or a viscosity of 12 mPa·s or more at a 5% aqueous solution at 25° C. is disclosed.

25 Claims, 1 Drawing Sheet

(56) References Cited

FOREIGN PATENT DOCUMENTS

| | | |
|---|---|---|
| JP | 3140465 B2 | 3/2001 |
| JP | 2001-114736 A | 4/2001 |
| JP | 2005-162736 A | 6/2005 |
| JP | 2008-532953 A | 8/2006 |
| JP | 3815496 B2 | 8/2006 |
| JP | 5625855 B2 | 11/2014 |
| JP | 5849946 B2 | 2/2016 |
| KR | 10-0355130 B | 1/2003 |
| KR | 2005-0072809 A | 7/2010 |
| KR | 2005-0107298 A | 9/2011 |
| WO | 94/06414 A1 | 3/1994 |
| WO | 02/00622 A2 | 1/2002 |
| WO | 02/48134 A2 | 6/2002 |
| WO | 2004/041276 A1 | 5/2004 |
| WO | 2009/019599 A2 | 2/2009 |
| WO | 2009/052353 A2 | 4/2009 |
| WO | 2010/038690 A1 | 4/2010 |

OTHER PUBLICATIONS

Chinese Patent Application No. 200980138691.9, first Office Action, dated Jun. 18, 2013, 14 pages (English translation).
Chinese Patent Application No. 200980138691.9, second Office Action, dated Jun. 18, 2013, 13 pages (English translation).
Decision of the Rejection, dated Jul. 3, 2015, CN Patent Application No. 200980138691.9, 43 pages (includes English translation).
Extended Search Report, dated Oct. 30, 2014, EP application No. 09 81 7723, 5 pages.
Final Office Action, dated May 17, 2013, U.S. Appl. No. 13/073,721.
Final Office Action, dated Nov. 21, 2013, U.S. Appl. No. 13/073,677.
Hercules Incorporated, "Klucel Hydroxypropylcellulose, Physical and Chemical Properties," Aqualon Division, http://www.brenntagspecialties.com/en/downloads/product/multi_market_principals/aqualon/klucel_hpc_booklet.pdf, 2001, 26 pages.
Intellectual Property Office of the Philippines; Subsequent Substantive Examination Report; PH Application No. 1/2011/500628; 3 pages; dated Jan. 11, 2016.
International Search Report of Application No. PCT/JP2009/066742 dated Nov. 10, 2009.
Ishikawa et al., "Preparation of rapidly disintegrating tablet using new types of microcrystalline cellulose (PH-M series) and low-substituted-hydroxypropylceliulose or spherical sugar granules by direct compression method," Chem. Pharm. Bull. 49(2) 134-139, 2001.
Israeli Patent Application No. 212033, First Substantive Examination Report, 4 pages (English translation).
Japanese Patent Application No. 2010-531838, first Office Action, dated Oct. 12, 2010, 8 pages (English translation).
Japanese Patent Application No. 2010-531838, first Office Action, dated Dec. 28, 2010, 4 pages (English translation).
Korean Patent Application No. 10-2011-7009897, Notice of Final Rejection, dated Nov. 17, 2014 (with English translation) 6 pages.
Korean Patent Application No. 10-2011-7009897, Notice of Preliminary Rejection, dated Mar. 20, 2014, 10 pages (includes English translation).
Mexican Institute of Industrial Property; First Office Action from Examiner; MX Application No. MX/a/2011/003445; 7 pages; dated Mar. 1, 2016.
Michel et al.,The Pharmacokinetc Profile of Tamsulosin Oral Controlled Absorption System (OCAS®), 2005, European Urology Supplements, vol. 4, pp. 15-24.
MX Application No. MX/a/2011/003445, Second Office Action dated Sep. 2, 2016, 2 pgs. (English translation 3 pgs.).
Non-Final Office Action; U.S. Appl. No. 14/584,933 dated Nov. 17, 2016, 17 pgs.
Office Action, dated May 13, 2013, U.S. Appl. No. 13/073,677.
Office Action, dated Oct. 18, 2012, U.S. Appl. No. 13/073,721.
Office Action, dated Sep. 17, 2012, U.S. Appl. No. 13/073,677.

PH Patent Application No. 1/2011/500628, Second Examination Report (Office Action), dated May 26, 2014, 2 pages.
Philippines Patent Application No. 1/2011/500628, Examination Report, dated Jul. 18, 2013, 2 pages.
Reexamination Notice, dated Jan. 30, 2015, Chinese Patent Application No. 200980138691.9, 14 pages (includes English translation).
Russia Patent Application No. 2011117274/15, Office Action, dated Mar. 6, 2013, 6 pages (English translation).
Shin-Etsu Chemical Co., Ltd, "Low-substituted hydroxypropyl cellulose NF, L-HPC" http://www.elementoorgankia.ru/files/lhpc.pdf, Cellulose & Pharmaceutical Department, 23 pages, accessed on Jun. 30, 2014.
U.S. Non—Final Office Action, U.S. Appl. No. 13/073,721, dated Jul. 30, 2014, 24 pages.
Indonesian Patent Application No. W00201101572, First Office Action dated Aug. 1, 2018, 4 pages.
Andersson, et al; Pharmacological treatment of overactive bladder: report from the International Consultation on Incontinence; Current Opinion in Urology; 2009; 19:380-394.
Benner et al; Patent-reported reasons for discontinuing overactive bladder medication; Journal Complication; 2009, BJU International; 105; 1276-1282.
Non-final Office Action; U.S. Appl. No. 14/584,933; dated Jan. 19, 2018.
The U.S. Patent and Trademark Office; Final Office Action in U.S. Appl. No. 14/584,933 dated Jul. 18, 2017.
D'Souza, et al; Persistence, Adherence, and Switch Rates Among Extended-Release and Immediate-Release Over Active Bladder Medications in a Regional Managed Care Plan; JMCP vol. 14, No. 3, Apr. 2008, pp. 291-301.
Controller of Patents, Indian Patent Office; Examination Report; dated May 29, 2017; Application No. 2738/CHENP/2011.
State Intellectual Property Office of the People's Republic of China; First Office Action; CN Patent Application No. 201510642287.2; dated Nov. 3, 2017.
European Patent Office; Communication Pursuant to Article 94(3) EPC dated Feb. 14, 2017 in Application No. 11 762 748.9-1468.
European Patent Office; Communication Pursuant to Article 114(2) EPC dated Feb. 2, 2017 in Application No. 11762748.9-1468/2554168.
BETMIGA® Tablets—Annex I, Summary of Product Characteristics; Dec. 2012.
Prescribing Information of MYRBETRIQ®; Aug. 2016.
European Medicines Agency—Assessment Report; dated Oct. 2012.
The U Co., Ltd; Petitioner's Brief; Korean Case No. 2017 Dang 569 Patent Invalidation Action re KR 10-1524164; Apr. 14, 2017.
Mexican Institute of Industrial Property; Communication of results of the examination on the merits; PCT Patent Application No. MX/a/2011/003445; dated Mar. 22, 2017.
State Intellectual Property Office of the People's Republic of China; Chinese Patent Application No. 201510642287.2; Notification of the Second Office Action; dated Jul. 25, 2018.
European Patent Office; First Official Communication pursuant to Article 94(3)EPC; Application No. 09817723.1-1114; dated Apr. 30, 2018.
European Patent Office; Third Party Observation—Communication pursuant to Rule 114(2)EPC; Application No. 09817723.1-1114; dated May 8, 2018.
Final Office Action dated Jan. 23, 2019 in U.S. Appl. No. 14/584,933.
European Patent Office; Official Communication pursuant to Article 94(3)EPC in European Application No. 09817723.1 dated Dec. 20, 2018.
Summons to Attend Oral Proceedings in re Opposition to European Patent No. 2 554 168 B1 (Jul. 17, 2019).
"<711> Dissolution" in USP30-NF25, vol. 1; The United States Pharmacopeial Convention: Rockville, pp. 277-284 (May 2007).
Guidance for Industry: Food-Effect Bioavailability and Fed Bioequivalence Studies, pp. 1-9, 2 (Dec. 2002) (emphasis added).
Sathish Ummadi et al., "Overview on Controlled Release Dosage Form," 3(4) Int. J. Pharma Sci. 258-269 (2013).
Christer Tannergren et al., "Toward an Increased Understanding of the Barriers to Colonic Drug Absorption in Humans Implications for

(56) References Cited

OTHER PUBLICATIONS

Early Controlled Release Candidate Assessment," 6(1) Mol. Pharmaceutics 60-73 (Feb. 2009).
Marilyn N. Martinez et al., "A Mechanistic Approach to Understanding the Factors Affecting Drug Absorption: A Review of Fundamentals," 42 J. Clin. Pharmacol. 620-643 (2002).
"Colonic Drug Absorption and Metabolism," Bieck ed., pp. 21-22 (1993).
Center for Drug Evaluation and Research, Application Number: 202611orig1s000, Clinical Pharmacology and Biopharmaceutics Review(s)—Mirabegron, 218 pages (Mar. 2012).
Preliminary Office Action in Brazilian Application No. PI0919466-5 (dated Sep. 2, 2019).
Submission by Lederer & Keller Patentanwälte Partnerschaft mbB in re Opposition to European Patent No. 2 554 168 (Oct. 10, 2019).
Submission by Hexal AG in re Opposition to European Patent No. 2 554 168 (Oct. 10, 2019).
"Yamanouchi Shaklee Pharma Licenses OCAS Drug Delivery Technology from Yamanouchi Pharmaceutical Co., Ltd.," Pharmaceutical Online, pp. 1-2 (May 1999).
Submission by STADA Arzneimittel AG in re Opposition to European Patent No. 2 554 168 (Oct. 10, 2019).
Communication pursuant to Article 94(3) EPC in European Application No. 09817723.1 (dated Sep. 4, 2019).
Center for Drug Development Assistance, National Institute of Food and Drug Safety Evaluation 11-1470550-000003-08, Dec. 2009, 121 pages and 5 pages English translation, Korea.
Chapple, Christopher R., The Development of the Oral Controlled Absorption System (OCAS®): A New Improved Formulation of Tamsulosin, European Urology Supplements, 2005, pp. 1-4, vol. D4, Elsevier B.V., UK.
Takasu, T., et al., Effect of ®-2-(2-aminothiazol-4-yl)-4'-{2-[(2-hydroxy-2-phenylethyl)amino]ethyl} acetanilide (YM178), a novel selective beta3-adrenoceptor agonist, on bladder function, J Pharmacol Exp Ther., May 2007, p. 321-322, vol. 642-7, Epub 2007. (Abstract only).
Hoffmann Eitle, Letter to European Patent Office responding to Official Action dated Feb. 14, 2017 in European Patent Application No. 11 762 758.9, dated Aug. 2, 2017, 5 pages.
clinicaltrials.gov, Pharmacokinetics of Oral Mirabegron With Different Release Rates Versus Intravenous (IV) Mirabegron, U.S. National Library of Medicine, Jul. 2013, 6 pages.
clinicaltrials.gov, History of Changes for Study: NCT00940121, Pharmacokinetics of Oral Mirabegron With Different Release Rates Versus Intravenous (IV) Mirabegron, U.S. National Library of Medicine, Jul. 2013, 7 pages.
Anlage A with Translation of the evidence during Opposition proceeding from opponent Notice of Opposition from STADA Arzneimittel AG dated Oct. 24, 2018 (99 pages) See #33 below.
Mauger et al., Intrinsic Dissolution Performance Testing of the USP Dissolution Apparatus 2 (Rotating Paddle) Using Modified Salicylic Acid Calibrator Tablets: Proof of Principle, Dissolution Technologies, Aug. 2003, pp. 6-15.
Andersson, Karl-Erik, Prospective Pharmacologic Therapies for the Overactive Bladder, Therapeutic Advances in Urology, 2009, 1(2) 71-83.
Dressman, et al., Oral Drug Absorption Prediction and Assessment, Drugs and the Pharmaceutical Sciences, 2000, Pages Preface, 183-228, Marcel Dekker, Inc., New York, USA.
Skelly et al., In Vitro and In Vivo Testing and Correlation for Oral Controlled/Modified Release Dosage Forms. Report of the $2^{nd}$ Workshop Held Dec. 1988, Washington, DC, U.S.A., Journal of Controlled Release, 1990, pp. 95-106, vol. 14, Elsevier Science Publishers B.V., Amsterdam, The Netherlands.
The European Agency for the Evaluation of Medicinal Products, Note for Guidance on Modified Release Oral and Transdermal Dosage Forms: Section II (Pharmacokinetic and Clinical Evaluation), Jul. 1999, 12 pages, London.

Lachman et al., Sustained Release Dosage Forms, The Theory and Practice of Industrial Pharmacy, $3^{rd}$ Edition, Chapter 14, Aug. 10, 2011, pp. 430-456.
Chapple et al., "Add-on" Tolterodine Extended Release Improves Overactive Bladder Symptoms in Men Receiving Alpha-Blocker Therapy, Eur Urol Suppl 2008; 7(3):239, Abstract 674.
Andersson et al., Pharmacological Treatment of Overactive Bladder: Report from the International Consultation on Incontinence, Current Opinion in Urology, 2009, pp. 380-394, vol. 19, Wolfers Klower Health.
clinicaltrials.gov, History of Changes for Study: NCT00662909, Study to Test the Efficacy and Safety of the Beta-3 Agonist YM178 in Patients with Symptoms of Overactive Bladder, U.S. National Library of Medicine, Nov. 2017, 8 pages.
clinicaltrials.gov, History of Changes for Study: NCT00912964, A Study to Test the Efficacy and Safety of the Beta-3 Agonist YM178 in Subjects with Symptoms of Overactive Bladder, U.S. National Library of Medicine, Nov. 2017, 8 pages.
clinicaltrials.gov, History of Changes for Study: NCT00689104, Study to Test the Efficacy and Safety of the Beta-3 Agonist YM178 in Subjects with Symptoms of Overactive Bladder, U.S. National Library of Medicine, Nov. 2017, 8 pages.
clinicaltrials.gov, History of Changes for Study: NCT00940121, Pharmacokinetics of Oral Mirabegron With Different Release Rates Versus Intravenous (IV) Mirabegron, U.S. National Library of Medicine, Jul. 2013, 8 pages.
clinicaltrials.gov, History of Changes for Study: NCT00965926, A Study to Investigate the Food Effect on the Pharmacokinetics of YM178 in Healthy, Non-elderly Volunteers, U.S. National Library of Medicine, Jul. 2013, 6 pages.
clinicaltrials.gov, History of Changes for Study: NCT00939757, Study of the Effect of Food on the Pharmacokinetics of Mirabegron, U.S. National Library of Medicine, Jul. 2013, 6 pages.
Bikiaris et al., New Aspects in Sustained Drug Release Formulations, Recent Patents on Drug Delivery & Formulation, 2007, pp. 201-213, vol. 1, No. 3, Bentham Science Publishers Ltd., Greece.
Wen et al., Oral Controlled Release Formulation Design and Drug Delivery, Theory to Practice, 2010, Pages preface and 1-9, John Wiley & Sons, Inc.
Siepmann et al., Polymer Blends for Controlled Release Coatings, Journal of Controlled Release, 2008, pp. 1-15, vol. 125, Elsevier B.V.
Gupta et al., Recent Trends in Oral Drug Delivery: A Review, Recent Patents on Drug Delivery & Formulation, 2009, pp. 162-173, vol. 3, Bentham Science Publishers Ltd.
Notice of Opposition to a European Patent, Patent No. EP2554168 to Astellas Pharma Inc., Opponent Hexal AG, Dated Oct. 24, 2018.
Notice of Opposition to a European Patent, Patent No. EP2554168 to Astellas Pharma Inc., Opponent STADA Arzneimittel AG, Dated Oct. 24, 2018.
Notice of Opposition to a European Patent, Patent No. EP2554168 to Astellas Pharma Inc., Opponent Alfred E. Tiefenbacher (GmbH & Co. KG), Dated Oct. 30, 2018.
Notice of Opposition to a European Patent, Patent No. EP2554168 to Astellas Pharma Inc., Opponent Lederer & Keller Patentanwalte Partnerschaft mbB, Dated Oct. 24, 2018.
Decision of Rejection in Chinese Application No. 201510642287.2 (dated Nov. 5, 2019).
European Patent Office; Official Communication pursuant to Rule 114(2) EPC in European Application No. 09817723.1 dated Jan. 10, 2019.
Amendment submitted dated May 30, 2012 by Applicant in U.S. Appl. No. 12/568,313—identified as T1 in the Official Communication cited herein.
Amendment submitted dated Aug. 26, 2013 by Applicant in U.S. Appl. No. 12/568,313—identified as T2 in the Official Communication cited herein.
Response to Communication Pursuant to Art. 94(3) EPC in European Application No. 09817723.1 (dated May 13, 2020).
Mitsuru Hashida (ed.), "Design and Evaluation of Formulations for Oral Administration," pp. 33, 35, 293-294 (Feb. 1995) (Exhibit A1).

(56) References Cited

OTHER PUBLICATIONS

A. Dokoumetzidis et al., "IVIVC of Controlled Release Formulations: Physiological—Dynamical Reasons for Their Failure," 129 J. Control. Release 76 (2008) (Exhibit A2).
Guidelines for the Design and Evaluation of Oral Prolonged Release Dosage Forms, Pharmaceutical Affairs Council, Ministry of Health and Welfare, Japan, (1), No. 5, pp. 1-4 (Mar. 1988) (Exhibit A3).
Idada Sadao et al. (eds.), "Comprehensive Techniques for Development System of New Formulations, Volume for Bases and Additive," pp. 424-429 (Jul. 1985) (Exhibit A4).
Kazuhiro Sako, "Formulations and Particle Design: Design of Novel Oral Controlled-Release System (OCAS) for Continuous Drug Absorption," 14(6) Pharm Tech Japan 85-98 (Jun. 1998) (Exhibit A5).
Hiroyasu Ogata, "1. Pharmacokinetics: Absorption," 30 (3) Jpn. J. Clin. Pharmacol. Ther. 617, 619 (May 1999) (Exhibit A9).
Written Demand for Trial for Invalidation of Japanese Patent No. 5849946 (dated Apr. 2020).
Non-Final Office Action in U.S. Appl. No. 14/584,933 (dated Jun. 10, 2020).
Response to Communication Pursuant to Rules 70(2) and 70a(2) EPC in European Application No. 11762748.9 (dated Nov. 2015).
Response to Communication Pursuant to Art. 94(3) EPC and Third Party Observations in European Application No. 11762748.9 (dated Aug. 2, 2017).
Observations in Response to Oppositions to European Patent No. 2 554 168 B1 (Mar. 25, 2019).
Response to Summons in Oppositions to European Patent No. 2 554 168 B1 (Oct. 10, 2019).
Response to Submissions of Opponents in Oppositions to European Patent No. 2 554 168 B1 (Oct. 18, 2019).
Decision in Oppositions and Oral Proceeding Minutes in European Patent No. 2 554 168 B1 (Mar. 2, 2020).
Response to Communication Pursuant to Rules 70(2) and 70a(2) EPC in European Application No. 09817723.1 (dated May 18, 2015).
Response to Communication Pursuant to Art. 94(3) EPC and Third Party Observations in European Application No. 09817723.1 (dated Aug. 28, 2018).
Response to Communication Pursuant to Art. 94(3) EPC and Third Party Observations in European Application No. 09817723.1 (dated May 20, 2019).
Response to Communication Pursuant to Art. 94(3) EPC in European Application No. 09817723.1 (dated Mar. 13, 2020).
Communication Pursuant to Art. 94(3) EPC in European Application No. 09817723.1 (dated Apr. 2, 2020).
Yoshinobu Yamazaki et al., "Species Differences in the Distribution of β3-Adrenoceptor Subtypes in Bladder Smooth Muscle," 124 Brit. J. Pharmacol. 593-599 (1998).
Osamu Yamaguchi, "β3-Adrenoceptors in Human Detrusor Muscle", 59 (Suppl. 5A) Urology 25-29 (2002).
Peter G. Welling, "Effects of Food on Drug Absorption," 16 Annu. Rev. Nutr. 383-415 (1996).
Nobuyuki Tanaka et al., "β3-Adrenoceptor Agonists for the Treatment of Frequent Urination and Urinary Incontinence: 2-[4-(2-{[(1S,2R)-2-Hydroxy-2-(4-hydroxyphenyl)-1-methylethyl]amino}ethyl)phenoxy]-2-methylpropionic Acid," 9 Bioorgan. Med. Chem. 3265-3271 (2001).
Nobuyuki Tanaka et al., "Discovery of Novel N-Phenylglycine Derivatives as Potent and Selective β3-Adrenoceptor Agonists for the Treatment of Frequent Urination and Urinary Incontinence," 44 J. Med. Chem. 1436-1445 (Apr. 2001).
Hiroo Takeda et al., "Role of the β3-Adrenoceptor in Urine Storage in the Rat: Comparison between the Selective β3-Adrenoceptor Agonist, CL316,243, and Various Smooth Muscle Relaxants," 293 J. Pharmacol. Exp. Ther. 939-945 (2000).
Brahma N. Singh, "Effects of Food on Clinical Pharmacokinetics," 37(3) Clin. Pharmacokinet. 213-255 (Sep. 1999).
Paul Abrams et al., "The Standardisation of Terminology in Lower Urinary Tract Function: Report from the Standardisation Sub-Committee of the International Continence Society," 21 Neurourol. Urodyn. 167-178 (2002).
K.-E. Andersson, "Overactive Bladder—Pharmacological Aspects," 210 Scand. J. Urol. Nephrol. Suppl. 72-81 (2002).
Richard J. Bastin et al., "Salt Selection and Optimisation Procedures for Pharmaceutical New Chemical Entities," 4(5) Org. Process Res. Dev. 427-435 (2000).
David P. Benziger et al., "Differential Effects of Food on the Bioavailability of Controlled-Release Oxycodone Tablets and Immediate-Release Oxycodone Solution," 85(4) J. Pharm. Sci. 407-410 (1996).
Harry G. Brittain, "Methods for the Characterization of Polymorphs and Solvates," Ch. 6 in Polymorphism in Pharmaceutical Solids, pp. 227-278 (1999).
Artur Burger, "The Relevance of Polymorphism," in Topics in Pharmaceutical Sciences 1983, pp. 347-358 (1983).
Stephen R. Byrn, Solid-State Chemistry of Drugs, pp. 6-11 (1982).
Stephen Bym et al., "Pharmaceutical Solids: A Strategic Approach of Regulatory Considerations," 12(7) Pharm. Res. 945-954 (1995).
Mino R. Caira, "Crystalline Polymorphism of Organic Compounds," in Topics in Current Chemistry, vol. 198, pp. 163-208 (1999).
Jens T. Carstensen, "Preformulation," Ch. 7 in Modem Pharmaceutics 213-237 (1996).
Drug Data Report, 21(7), p. 619.
Daniel S. Elliott et al., "Medical Management of Overactive Bladder," 76(4) Mayo Clin Proc. 353-355 (Apr. 2001).
Guideline for Industry: Guideline for Submitting Supporting Documentation for the Manufacture of and Controls for Drug Products, Center for Drugs and Biologics, Food and Drug Administration, pp. 1-17 (Feb. 1987).
David Fleisher et al., "Drug, Meal and Formulation Interactions Influencing Drug Absorption After Oral Administration," 36(3) Clin. Pharmacokinet. 233-254 (Mar. 1999).
Takao Fujimura et al., "Expression and Possible Functional Role of the β3-Adrenoceptor in Human and Rat Detrusor Muscle," 161 J. Urol. 680-685 (1999).
Janice J. MacKichan et al., "Pharmacokinetic Considerations for Drug Delivery," Ch. 2 in Gibaldi's Drug Delivery Systems in Pharmaceutical Use, pp. 11-22 (2007).
Dharmesh H. Doshi, "Oral Delivery Systems," Ch. 3 in Gibaldi's Drug Delivery Systems in Pharmaceutical Use, pp. 23-41 (2007).
Philip L. Gould, "Salt Selection for Basic Drugs," 33(1-3) Int. J. Pharm. 201-217 (1986).
John Haleblian et al., "Pharmaceutical Applications of Polymorphism," 58(8) J. Pharm. Sci 911-929 (Aug. 1969).
Bruno C. Hancock et al., "Characteristics and Significance of the Amorphous State in Pharmaceutical Systems," 86(1) J. Pharm. Sci. 1-12 (Jan. 1997).
Y. Igawa et al., "Possible β3-Adrenoceptor-Mediated Relaxation of the Human Detrusor", 164 Acta Physiol Scand 117-118 (1998).
Rajendra K. Khankari et al., "Pharmaceutical Hydrates," 248 Thermochimica Acta 61-79 (1995).
Penelope A. Longhurst et al., "Pharmacological techniques for the in vitro study of the urinary bladder," 45 J. Pharmacol. Tox. Met. 91-108 (2001).
"Hydrates," in Encyclopedia of Pharmaceutical Technology, vol. 7, p. 393 (1993).
Donna J. Sellers et al., "Potential therapeutic targets for treatment of overactive bladder," 19 World J. Ural. 307-311 (2001).
Technical Examination Report in Brazilian Application No. PI0919466-5 (dated Jul. 10, 2020).
Technical Examination Report in Brazilian Application No. BR122019026041-9 (dated Jul. 10, 2020).

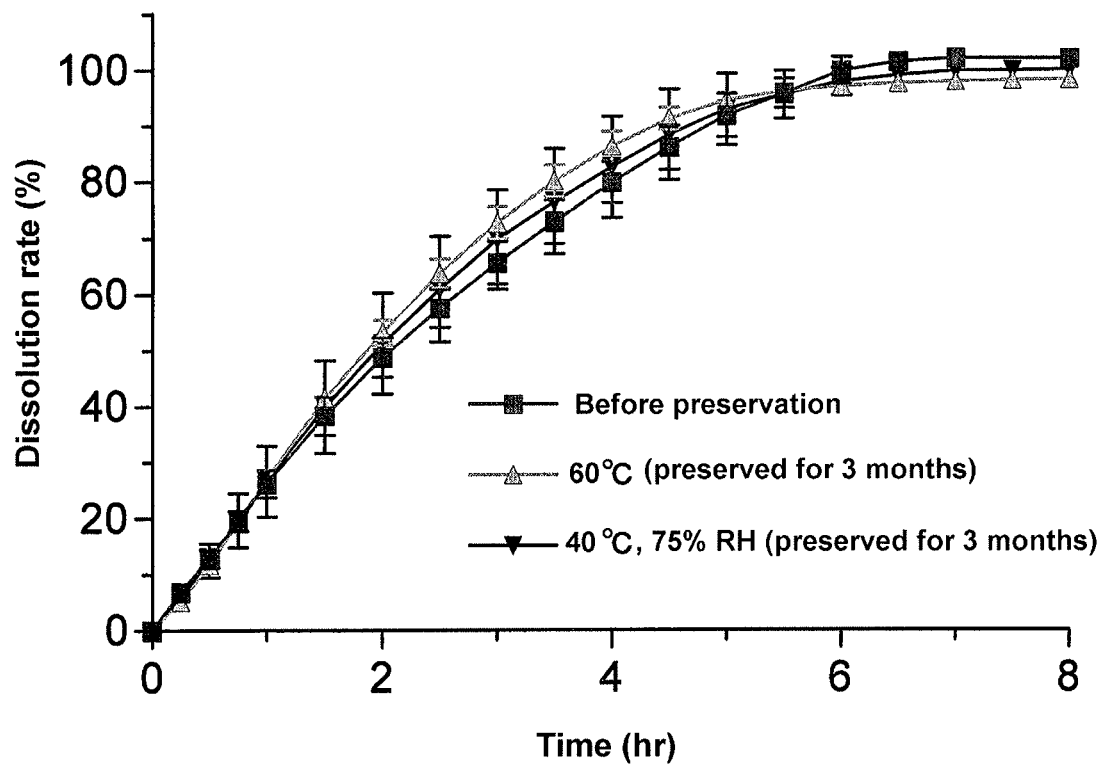

PHARMACEUTICAL COMPOSITION FOR MODIFIED RELEASE

CROSS REFERENCE TO RELATED APPLICATIONS

The present application is a continuation of U.S. patent application Ser. No. 12/568,313, filed Sep. 28, 2009, which application claims the benefit of priority to U.S. Patent Application No. 61/101,338, filed Sep. 30, 2008, the teachings of which are hereby incorporated by reference.

TECHNICAL FIELD

The present invention relates to a pharmaceutical composition for modified release capable of reducing food effects, which are observed in conventional tablets, by combining an active ingredient with specific ingredients to control a releasing rate of the active ingredient.

More particularly, the present invention relates to a pharmaceutical composition comprising (R)-2-(2-aminothiazol-4-yl)-4'-[2-[(2-hydroxy-2-phenylethyl)amino]ethyl]acetic acid anilide or a pharmaceutically acceptable salt thereof, an additive which ensures penetration of water into the pharmaceutical composition (hereinafter sometimes referred to as a hydrophilic base), and a polymer which forms a hydrogel, in which the changes in AUC and Cmax caused by the intake of food can be decreased by controlling a releasing rate of the active ingredient.

BACKGROUND ART (R)-2-(2-aminothiazol-4-yl)-4'-[2-[(2-hydroxy-2-phenylethyl)amino]ethyl]acetic acid anilide has been created by Astellas Pharma Inc., and it has been reported that this compound has not only both an activity of promoting insulin secretion and an activity of enhancing insulin sensitivity, but also an antiobestic activity and an antihyperlipemic activity based on an activity of selectively stimulating a β3 receptor, and is useful in treating diabetes (see, for example, patent literature 1).

Further, it has been reported that the compound can be used as a therapeutic agent for overactive bladder, such as overactive bladder accompanied by prostatic hyperplasia, or overactive bladder accompanied by urinary urgency, urinary incontinence, and urinary frequency (see, for example, patent literature 2).

A clinical trial of (R)-2-(2-aminothiazol-4-yl)-4'-[2-[(2-hydroxy-2-phenylethyl)amino]ethyl]acetic acid anilide in the form of conventional formulations revealed disadvantages, for example, that pharmacokinetic data unexpectedly varied according to the presence or absence of the intake of food (not published). For example, the rate of decrease of Cmax in a fed state was 67%, and the rate of decrease of AUC in the fed state was 47%, in comparison with those in a fasted state. In this case, Cmax in the fasted state was three times higher than that in the fed state. These problems are considered to be raised by, for example, the changes in pharmacokinetics caused by food, and therefore, the development of a formulation capable of avoiding the effects by food intake is desired.

As a technique of preparing a formulation for modified release, a hydrogel sustained release tablet containing an additive which ensures penetration of water into the tablet, and a hydrogel-forming polymer is disclosed (see, for example, patent literature 3).

However, patent literature 3 does not refer to (R)-2-(2-aminothiazol-4-yl)-4'-[2-[(2-hydroxy-2-phenylethyl)amino]ethyl]acetic acid anilide, and further improvements are needed to produce a pharmaceutical composition.

CITATION LIST

Patent Literature

[patent literature 1] International Publication No. WO 99/20607 (Example 41)
[patent literature 2] International Publication No. WO 2004/041276
[patent literature 3] International Publication No. WO 94/06414

SUMMARY OF INVENTION

Technical Problem

An object of the present invention is to provide a pharmaceutical composition for modified release comprising (R)-2-(2-aminothiazol-4-yl)-4'-[2-[(2-hydroxy-2-phenylethyl)amino]ethyl]acetic acid anilide or a pharmaceutically acceptable salt thereof, in which the pharmaceutical composition has efficacy the same as or higher than those of conventional formulations and has no limitations on food intake, and a process of manufacturing the pharmaceutical composition.

Solution to Problem

The elimination half-life ($T_{1/2}$) of (R)-2-(2-aminothiazol-4-yl)-4'-[2-[(2-hydroxy-2-phenylethyl)amino]ethyl]acetic acid anilide is long (approximately 18 to 24 hours), and thus, a formulation thereof for modified release is not necessarily needed to maintain its blood level. Taking into consideration the results of the clinical trial described above, the present inventors conducted intensive studies to design the formulation by paying attention to the control of a release rate of the drug from a formulation to the extent that the release is not affected by food intake or the like, rather than the addition of release control.

On the basis of blood concentration profiles (in a fasted state/after the intake of food) after administration of a conventional formulation (rapid release formulation), the absorption rate of the drug in a fed state was calculated by a deconvolution method to predict continuous absorption for about 4 hours. The present inventors considered from this result that a formulation capable of continuous drug release for 4 hours or more would be able to reduce the effects by food, because the drug release from the formulation would become the rate-limiting step for absorption.

The present inventors carried out a clinical trial in human using three types of formulations in which the release rate of the drug was controlled (Time when the release percentage of the drug from the unit formulation was 80% (T80%)=4 hr, 6 hr, and 10 hr), and found that all formulations could reduce the effects by food, to complete the present invention.

It is generally known that the retention time in the stomach and the release rate of formulations for modified release vary according to the presence or absence of food intake, and as a result, there is a possibility that blood concentration profiles is changed. However, surprisingly, when using this formulation, the change of the blood concentration profiles was small in the presence or absence of food intake.

The present invention is characterized by providing a pharmaceutical composition for modified release which is not affected by the effects of food intake and exhibits a decreased change in AUC or Cmax.

The present invention provides:

[1] a pharmaceutical composition for modified release, comprising (1) (R)-2-(2-aminothiazol-4-yl)-4'-[2-[(2-hydroxy-2-phenylethyl)amino]ethyl]acetic acid anilide, or a pharmaceutically acceptable salt thereof, (2) at least one additive which ensures penetration of water into the pharmaceutical composition and which has a solubility such that the volume of water required for dissolving 1 g of the additive is 10 mL or less, and (3) a hydrogel-forming polymer having an average molecular weight of approximately 100,000 or more, or a viscosity of 12 mPa·s or more at a 5% aqueous solution at 25° C.;

[2] the pharmaceutical composition for modified release of [1], wherein the additive which ensures penetration of water into the pharmaceutical composition is one compound, or two or more compounds selected from the group consisting of polyethylene glycol, polyvinylpyrrolidone, D-mannitol, D-sorbitol, xylitol, lactose, sucrose, anhydrous maltose, D-fructose, dextran, glucose, polyoxyethylene hydrogenated castor oil, polyoxyethylene polyoxypropylene glycol, polyoxyethylene sorbitan higher fatty acid ester, sodium chloride, magnesium chloride, citric acid, tartaric acid, glycine, β-alanine, lysine hydrochloride, and meglumine;

[3] the pharmaceutical composition for modified release of [2], wherein the additive which ensures penetration of water into the pharmaceutical composition is one compound, or two or more compounds selected from the group consisting of polyethylene glycol, polyvinylpyrrolidone, D-mannitol, lactose, sucrose, sodium chloride, and polyoxyethylene polyoxypropylene glycol;

[4] the pharmaceutical composition for modified release of any one of [1] to [3], wherein an amount of the additive which ensures penetration of water into the pharmaceutical composition is 5% by weight to 75% by weight with respect to the total weight of the pharmaceutical composition;

[5] the pharmaceutical composition for modified release of [4], wherein an amount of the additive which ensures penetration of water into the pharmaceutical composition is 5% by weight to 70% by weight with respect to the total weight of the pharmaceutical composition;

[6] the pharmaceutical composition for modified release of any one of [1] to [5], wherein the hydrogel-forming polymer is one compound, or two or more compounds selected from the group consisting of polyethylene oxide, hydoxypropyl methylcellulose, hydroxypropyl cellulose, carboxymethyl cellulose sodium, hydroxyethyl cellulose, and a carboxyvinyl polymer;

[7] the pharmaceutical composition for modified release of [6], wherein the hydrogel-forming polymer is one compound, or two or more compounds selected from the group consisting of polyethylene oxide, hydroxypropyl methylcellulose, and hydroxypropyl cellulose;

[8] the pharmaceutical composition for modified release of any one of [1] to [7], wherein an amount of the hydrogel-forming polymer is 1% by weight to 70% by weight with respect to the total weight of the pharmaceutical composition;

[9] the pharmaceutical composition for modified release of any one of [1] to [8], further comprising an antioxidant;

[10] the pharmaceutical composition for modified release of [9], wherein the antioxidant is one compound, or two or more compounds selected from the group consisting of butyl hydroxytoluene, propyl gallate, and sodium ascorbate;

[11] the pharmaceutical composition for modified release of claim 10, wherein the antioxidant is butyl hydroxytoluene;

[12] the pharmaceutical composition for modified release of any one of [9] to [11], wherein an amount of the antioxidant is 0.025% by weight to 0.25% by weight;

[13] the pharmaceutical composition for modified release of any one of [1] to [12], further comprising a stabilizer;

[14] the pharmaceutical composition for modified release of [13], wherein the stabilizer is one compound, or two or more compounds selected from the group consisting of yellow ferric oxide, red ferric oxide, and black iron oxide;

[15] the pharmaceutical composition for modified release of [14], wherein the stabilizer is yellow ferric oxide and/or red ferric oxide;

[16] the pharmaceutical composition for modified release of any one of [13] to [15], wherein an amount of the stabilizer is 0.05% by weight to 1% by weight;

[17] a process of manufacturing a pharmaceutical composition for modified release, characterized by comprising mixing (1) (R)-2-(2-aminothiazol-4-yl)-4'-[2-[(2-hydroxy-2-phenylethyl)amino]ethyl]acetic acid anilide, or a pharmaceutically acceptable salt thereof with (2) at least one additive which ensures penetration of water into the pharmaceutical composition and which has a solubility such that the volume of water required for dissolving 1 g of the additive is 10 mL or less and (3) a hydrogel-forming polymer having an average molecular weight of approximately 100,000 or more, or a viscosity of 12 mPa·s or more at a 5% aqueous solution at 25° C., wherein an amount of the additive is 5% by weight to 75% by weight with respect to the total weight of the pharmaceutical composition, and an amount of the hydrogel-forming polymer is 1% by weight to 70% by weight with respect to the total weight of the pharmaceutical composition;

[18] the process of [17], wherein the additive which ensures penetration of water into the pharmaceutical composition is one compound, or two or more compounds selected from the group consisting of polyethylene glycol, polyvinylpyrrolidone, D-mannitol, D-sorbitol, xylitol, lactose, sucrose, anhydrous maltose, D-fructose, dextran, glucose, polyoxyethylene hydrogenated castor oil, polyoxyethylene polyoxypropylene glycol, polyoxyethylene sorbitan higher fatty acid ester, sodium chloride, magnesium chloride, citric acid, tartaric acid, glycine, β-alanine, lysine hydrochloride, and meglumine; and

[19] the process of [17] or [18], wherein the hydrogel-forming polymer is one compound, or two or more compounds selected from the group consisting of polyethylene oxide, hydoxypropyl methylcellulose, hydroxypropyl cellulose, carboxymethyl cellulose sodium, hydroxyethyl cellulose, and a carboxyvinyl polymer.

As formulation techniques for reducing or avoiding the changes in pharmacokinetics such as AUC or Cmax accompanied by food intake, a formulation technique concerning a sustained-release pharmaceutical composition containing tamsulosin hydrochloride is disclosed (see Japanese Unexamined Patent Publication (Kokai) No. 2005-162736 and Japanese Unexamined Patent Publication (Kokai) No. 2005-162737). This formulation technique is limited to tamsulosin, and applied to a formulation containing the drug at a low dose (0.4 mg per unit formulation). This formulation enables to control the release of tamsulosin therefrom by being mainly composed of a sustained-release base. By contrast, the pharmaceutical composition contains the drug at a high dose (i.e., high content per unit formulation), and it is considered difficult to control the release rate of the drug from a formulation containing the sustained-release base at a low content, and therefore, the present invention is technically quite different from the formulation disclosed in these references.

Effects of Invention

According to the present invention, a pharmaceutical composition for modified release which has no limitations on food intake and is stable (for example, reduction of changes in a sequential dissolution profile) can be provided.

Further, a pharmaceutical composition for modified release in which AUC is not reduced can be provided.

With respect to a conventional formulation, the rate of decrease of Cmax in the fed state was 67% in comparison with that in a fasted state. By contrast, with respect to the pharmaceutical composition for modified release of the present invention, the rate of decrease of Cmax in the fed state was 42% in comparison with that in a fasted state, and this result showed that reduction of Cmax caused by food intake could be significantly alleviated by forming its formulation into the pharmaceutical formulation for modified release.

BRIEF DESCRIPTION OF DRAWINGS

The FIGURE is a graph showing dissolution profiles of the pharmaceutical composition for modified release prepared in Example 11, and the time courses thereof.

DESCRIPTION OF EMBODIMENTS

The pharmaceutical composition for modified release of the present invention will be explained hereinafter.

The term "rapid release formulation (conventional formulation)" as used herein means a formulation in which the dissolution rate of the drug from the formulation is 85% or more after 30 minutes from the beginning a dissolution test, which is carried out in accordance with a dissolution test (paddle method) described in the United States Pharmacopoeia under the conditions that 900 mL of an appropriate test fluid (such as a USP buffer, pH 6.8) is used and the paddle rotation speed is 100 rpm. Alternatively, the term means a formulation in which the dissolution rate of the drug from the formulation is 85% or more after 30 minutes from the beginning a dissolution test, which is carried out in accordance with a dissolution test, method 2 described in the Japanese Pharmacopoeia under the conditions that 900 mL of an appropriate test fluid (such as a Mc. Ilvain buffer, pH 6.8) is used and the paddle rotation speed is 50 rpm.

The term "pharmaceutical composition for modified release" as used herein means a formulation in which the dissolution rate of the drug from the formulation is less than 85% after 30 minutes from the beginning a dissolution test carried out under the above conditions, and the drug release is controlled to the extent that the effects by food are reduced. More particularly, it is a formulation in which an additive (hydrophilic base) which ensures penetration of water into the formulation is combined with a polymer which forms a hydrogel.

The wording "the effects by food are reduced" as used herein means, for example, a 10% reduction, a 20% reduction in another embodiment, and a 30% reduction in still another embodiment, in comparison with Cmax of a conventional formulation. Alternatively, the term means, for example, a 10% reduction with respect to the rates of decrease of Cmax and AUC in administration after food intake, in comparison with Cmax and AUC in administration in the fasted state, a 20% reduction in another embodiment, and a 30% reduction in still another embodiment.

The rates of decrease of Cmax and AUC are calculated by the following equations:

$$Rd(Cmax)=[Cmax(FS)-Cmax(FI)]\times 100/Cmax(FS)$$

$$Rd(AUC)=[AUC(FS)-AUC(FI)]1\times 100/AUC(FS)$$

Rd(Cmax): Rate of decrease of Cmax (%)
Cmax(FS): Cmax in administration in the fasted state
Cmax(FI): Cmax in administration after food intake
Rd(AUC): Rate of decrease of AUC (%)
AUC(FS): AUC in administration in the fasted state
AUC(FI): AUC in administration after food intake The term "formulation in which the effects by food are reduced" as used herein means a formulation in which the dissolution rate of the drug from the formulation is 75% or less after 1.5 hours and 100% or less after 4 hours from the beginning a dissolution test, which is carried out under the above conditions [in accordance with a dissolution test (paddle method) described in the United States Pharmacopoeia under the conditions that 900 mL of an appropriate test fluid (such as a USP buffer, pH 6.8) is used and the paddle rotation speed is 50 to 200 rpm]. In another embodiment, the term means a formulation in which the dissolution rate of the drug from the formulation is 75% or less after 1.5 hours and 75% or more to 100% or less after 7 hours.

The term "stable" as used herein means that it is stable against, for example, heat, temperature, humidity, or light. More particularly, the term means that, for example, when a plastic bottle is filled with a pharmaceutical composition and sealed, and then, the bottle is preserved for three months under the conditions at 40° C. and 75% RH or at 60° C., the change in the dissolution rate at the point showing a dissolution rate of 50% is within ±5% or less. Alternatively, the term means that, for example, when a pharmaceutical composition is exposed to 1.2 million Lux·hr of light, the change in the dissolution rate at the point showing a dissolution rate of 50% is within ±5% or less.

(R)-2-(2-aminothiazol-4-yl)-4'-[2-[(2-hydroxy-2-phenylethyl)amino]ethyl]acetic acid anilide (hereinafter sometimes referred to as compound A) is represented by the following structural formula.

[Chem. 1]

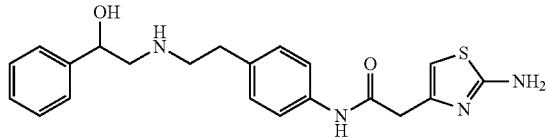

Compound A may be used in a free form which is not a salt, and may form a salt with an acid in other embodiments. Examples of such a salt include an acid addition salt with a mineral acid such as hydrochloric acid, hydrobromic acid, hydroiodic acid, sulfuric acid, nitric acid, phosphoric acid, or the like; and an acid addition salt with an organic acid such as formic acid, acetic acid, propionic acid, oxalic acid, malonic acid, succinic acid, fumaric acid, maleic acid, lactic acid, malic acid, citric acid, tartaric acid, carbonic acid, picric acid, methanesulfonic acid, ethanesulfonic acid, glutamic acid, or the like.

The dose of compound A may be appropriately selected in accordance with symptom, age, sex, and the like of the patient to be treated. The daily dose of compound A for oral administration to an adult is generally 0.01 to 100 mg/kg, which is administered once or divided into two to four doses per day.

The content of compound A per formulation is, for example, 1% by weight to 70% by weight, 5% by weight to 70% by weight in another embodiment, and 5% by weight to 50% by weight in still another embodiment. The content of compound A per formulation is 1 mg to 500 mg, and 10 mg to 200 mg in another embodiment.

It is necessary that the hydrogel-forming polymer used in the present invention can control the release rate of the drug, to the extent that the blood concentration profile of the drug is not affected by the presence or absence of food intake.

The molecular weight of the hydrogel-forming polymer is, for example, 100,000 or more, 100,000 to 8,000,000 in another embodiment, 100,000 to 5,000,000 in still another embodiment, and 100,000 to 2,000,000 in still another embodiment. The viscosity of the hydrogel-forming polymer is, for example, 12 mPa·s or more in a 5% aqueous solution at 25° C.; 12 mPa·s or more in a 5% aqueous solution at 25° C., and 40,000 mPa·s or less in a 1% aqueous solution at 25° C. in another embodiment; 400 mPa·s or more in a 2% aqueous solution at 25° C., and 7,500 mPa·s or less in a 1% aqueous solution at 25° C. in still another embodiment; and 400 mPa·s or more in a 2% aqueous solution at 25° C., and 5,500 mPa·s or less in a 1% aqueous solution at 25° C. in still another embodiment.

In the pharmaceutical composition for modified release of the present invention, the release period of time of the drug from the formulation can be arbitrarily controlled by adjusting the viscosity of the polymer which is used as the hydrogel-forming polymer.

The hydrogel-forming polymer used in the present invention is not particularly limited, so long as the release of the drug can be controlled to the extend that the effects of food on compound A may be reduced. Examples of the hydrogel-forming polymer include polyethylene oxide, hydroxypropyl methylcellulose, hydroxypropyl cellulose, carboxymethyl cellulose sodium, hydroxyethyl cellulose, and carboxyvinyl polymers. Examples of the hydrogel-forming polymer in another embodiment include polyethylene oxide, hydroxypropyl methylcellulose, and hydroxypropyl cellulose.

Examples of polyethylene oxide (hereinafter sometimes referred to as PEO) include product names, Polyox WSR-308 [average molecular weight: 8,000,000, viscosity: 10,000-15,000 mPa·s (1% aqueous solution at 25° C.)], Polyox WSR-303 [average molecular weight: 7,000,000, viscosity: 7,500-10,000 mPa·s (1% aqueous solution at 25° C.)], Polyox WSR Coagulant [average molecular weight: 5,000,000, viscosity: 5,500-7,500 mPa·s (1% aqueous solution at 25° C.)], Polyox WSR-301 [average molecular weight: 4,000,000, viscosity: 1,650-5,500 mPa·s (1% aqueous solution at 25° C.)], Polyox WSR-N-60K [average molecular weight: 2,000,000, viscosity: 2,000-4,000 mPa·s (2% aqueous solution at 25° C.)], Polyox WSR-N-12K [average molecular weight: 1,000,000, viscosity: 400-800 mPa·s (2% aqueous solution at 25° C.)], Polyox WSR-1105 [average molecular weight: 900,000, viscosity: 8,800-17,600 mPa·s (5% aqueous solution at 25° C.)], Polyox WSR-205 [average molecular weight: 600,000, viscosity: 4,500-8,800 mPa·s (5% aqueous solution at 25° C.)], Polyox WSR-N-750 [average molecular weight: 300,000, viscosity: 600-1200 mPa·s (5% aqueous solution at 25° C.)], Polyox WSR-N-80 [average molecular weight: 200,000, viscosity: 55-90 mPa·s (5% aqueous solution at 25° C.)], and Polyox WSR-N-10 [average molecular weight: 100,000, viscosity: 12-50 mPa·s (5% aqueous solution at 25° C.)] (DOW).

Examples of hydoxypropyl methylcellulose (hereinafter sometimes referred to as HPMC) include product name Metolose 90SH50000 [viscosity in a 2% aqueous solution at 20° C.: 2,900-3,900 mPa·s], Metolose SB-4 (product name, Shin-Etsu Chemical Co., Ltd.) (viscosity in a 2% aqueous solution at 20° C.: approximately 4 mPa·S), TC-5RW (product name, Shin-Etsu Chemical Co., Ltd.) (viscosity in a 2% aqueous solution at 20° C.: approximately 6 mPa·S), TC-5S (product name, Shin-Etsu Chemical Co., Ltd.) (viscosity in a 2% aqueous solution at 20° C.: approximately 15 mPa·S), TC-5R (product name, Shin-Etsu Chemical Co., Ltd.) (viscosity in a 2% aqueous solution at 20° C.: approximately 6 mPa·S), TC-5M (product name, Shin-Etsu Chemical Co., Ltd.) (viscosity in a 2% aqueous solution at 20° C.: approximately 4.5 mPa·S), TC-5E (product name, Shin-Etsu Chemical Co., Ltd.) (viscosity in a 2% aqueous solution at 20° C.: approximately 3 mPa·S), Metolose 60SH-50 (product name, Shin-Etsu Chemical Co., Ltd.) (viscosity in a 2% aqueous solution at 20° C.: approximately 50 mPa·s), Metolose 65SH-50 (product name, Shin-Etsu Chemical Co., Ltd.) (viscosity in a 2% aqueous solution at 20° C.: approximately 50 mPa·s), Metolose 90SH-100 (product name, Shin-Etsu Chemical Co., Ltd.) (viscosity in a 2% aqueous solution at 20° C.: approximately 100 mPa·s), Metolose 90SH-100SR (product name, Shin-Etsu Chemical Co., Ltd.) (viscosity in a 2% aqueous solution at 20° C.: approximately 100 mPa·s), Metolose 65SH-400 (product name, Shin-Etsu Chemical Co., Ltd.) (viscosity in a 2% aqueous solution at 20° C.: approximately 400 mPa·s), Metolose 90SH-400 (product name, Shin-Etsu Chemical Co., Ltd.) (viscosity in a 2% aqueous solution at 20° C.: approximately 400 mPa·s), Metolose 65SH-1500 (product name, Shin-Etsu Chemical Co., Ltd.) (viscosity in a 2% aqueous solution at 20° C.: approximately 1,500 mPa·s), Metolose 60SH-4000 (product name, Shin-Etsu Chemical Co., Ltd.) (viscosity in a 2% aqueous solution at 20° C.: approximately 4,000 mPa·s), Metolose 65SH-4000 (product name, Shin-Etsu Chemical Co., Ltd.) (viscosity in a 2% aqueous solution at 20° C.: approximately 4,000 mPa·s), Metolose 90SH-4000 (product name, Shin-Etsu Chemical Co., Ltd.) (viscosity in a 2% aqueous solution at 20° C.: approximately 4,000 mPa·s), Metolose 90SH-4000SR (product name, Shin-Etsu Chemical Co., Ltd.) (viscosity in a 2% aqueous solution at 20° C.: approximately 4,000 mPa·s), Metolose 90SH-15000 (product name, Shin-Etsu Chemical Co., Ltd.) (viscosity in a 2% aqueous solution at 20° C.: approximately 15,000 mPa·s), Metolose 90SH-15000SR (product name, Shin-Etsu Chemical Co., Ltd.) (viscosity in a 2% aqueous solution at 20° C.: approximately 15,000 mPa·s), and Metolose 90SH-30000 (product name, Shin-Etsu Chemical Co., Ltd.) (viscosity in a 2% aqueous solution at 20° C.: approximately 30,000 mPa·s).

Examples of hydroxypropyl cellulose (hereinafter sometimes referred to as HPC) include HPC-SSL (product name, Nippon Soda Co., Ltd.) (viscosity in a 2% aqueous solution at 20° C.: 2.0-2.9 mPa·S), HPC-SL (product name, Nippon Soda Co., Ltd.) (viscosity in a 2% aqueous solution at 20° C.: 3.0-5.9 mPa·S), HPC-L (product name, Nippon Soda Co., Ltd.) (viscosity in a 2% aqueous solution at 20° C.: 6.0-10.0 mPa·S), HPC-M (product name, Nippon Soda Co., Ltd.) (viscosity in a 2% aqueous solution at 20° C.: 150-400 mPa·S), and HPC-H (product name, Nippon Soda Co., Ltd.) (viscosity in a 2% aqueous solution at 20° C.: 1,000-4,000 mPa·S).

Examples of methylcellulose (hereinafter sometimes referred to as MC) include Metolose SM15 (product name, Shin-Etsu Chemical Co., Ltd.) (viscosity in a 2% aqueous solution at 20° C.: approximately 15 mPa·S), Metolose SM25 (product name, Shin-Etsu Chemical Co., Ltd.) (viscosity in a 2% aqueous solution at 20° C.: approximately 25 mPa·S), Metolose SM100 (product name, Shin-Etsu Chemical Co., Ltd.) (viscosity in a 2% aqueous solution at 20° C.: approximately 100 mPa·S), Metolose SM400 (product name, Shin-Etsu Chemical Co., Ltd.) (viscosity in a 2% aqueous solution at 20° C.: approximately 400 mPa·S), Metolose SM1500 (product name, Shin-Etsu Chemical Co., Ltd.) (viscosity in a 2% aqueous solution at 20° C.: approximately 1,500 mPa·S), and Metolose SM4000 (product name, Shin-Etsu Chemical Co., Ltd.) (viscosity in a 2% aqueous solution at 20° C.: approximately 4,000 mPa·S).

Examples of carboxymethyl cellulose sodium (hereinafter sometimes referred to as CMCNa) include product names, Sunrose F-30MC [viscosity: 250-350 mPa·s (1% aqueous solution at 25° C.)], Sunrose F-150MC [average molecular weight: 200,000, viscosity: 1,200-1,800 mPa·s (1% aqueous solution at 25° C.)], Sunrose F-600MC [viscosity: 6,000-8,000 mPa·s (1% aqueous solution at 25° C.)], Sunrose F-1000MC [average molecular weight: 420,000, viscosity: 8,000-12,000 mPa·s (the same)], Sunrose F-1400MC [viscosity: 12,000-15,000 mPa·s (1% aqueous solution at 25° C.)], and Sunrose F-300MC [average molecular weight: 300,000, viscosity: 2,500-3,000 mPa·s (the same)] (Nippon Paper Chemicals Co., Ltd.).

Examples of hydroxyethyl cellulose (hereinafter sometimes referred to as HEC) include product names, HEC DAICEL SE850 [average molecular weight: 1,480,000, viscosity: 2,400-3,000 mPa·s (1% aqueous solution at 25° C.)], and HEC DAICEL SE900 [average molecular weight: 1,560,000, viscosity: 4,000-5,000 mPa·s (1% aqueous solution at 25° C.)](Daicel chemical Industries, Ltd.).

Examples of carboxyvinyl polymers include Carbopol 71G (viscosity: 4,000-11,000 mPa·s), Carbopol 971P (viscosity: 4,000-11,000 mPa·s), Carbopol 981 (viscosity: 4,000-10,000 mPa·s), Carbopol 941 (viscosity: 4,000-10,000 mPa·s), Carbopol 934 (viscosity: 30,500-39,400 mPa·s), and Carbopol 934P (viscosity: 29,400-39,400 mPa·s)(B.F.-Goodrich Chemical).

These hydrogel-forming polymers may be used alone, or as an appropriate combination of two or more thereof. A combination of different lots may be used.

The content of the hydrogel-forming polymer is not particularly limited, so long as it is an amount to the extent that the blood concentration profile of the drug is not affected by the presence or absence of food intake. The content of the hydrogel-forming polymer is, for example, 1% by weight to 70% by weight with respect to the total weight of the formulation, and 3% by weight to 70% by weight in another embodiment. The content of the hydrogel-forming polymer is 5% by weight to 70% by weight with respect to the total weight of the formulation, 10% by weight to 60% by weight in another embodiment, and 10% by weight to 40% by weight in still another embodiment. The content of the hydrogel-forming polymer is 0.1% by weight to 1,000% by weight with respect to the weight of the drug, 1% by weight to 500% by weight in another embodiment, and 5% by weight to 300% by weight in still another embodiment.

A polymer of which the viscosity (before mixing) is beyond the specific range can be used as an appropriate combination with one or more other polymers, in case that the mixture obtained by mixing these plural polymers has a viscosity (as measured before the use) within the specific range.

In the additive which ensures penetration of water into the pharmaceutical composition of the present invention (hydrophilic base), the amount of water necessary to dissolve 1 g of the hydrophilic base at 20±5° C. is 10 mL or less, 6 mL or less in another embodiment, 5 mL or less in still another embodiment, and 4 mL or less in still another embodiment. When the hydrophilic base has a high solubility to water, the effect that allows water to penetrate into the formulation is high.

Examples of the hydrophilic base include water-soluble polymers, such as polyethylene glycol [PEG: for example, product names PEG 400, PEG 1500, PEG 4000, PEG 6000, and PEG 20000 (NOF Corporation)], polyvinyl pyrrolidone (PVP: for example, product name PVP K30 (BASF), and the like; sugar alcohols, such as D-mannitol, D-sorbitol, xylitol, and the like; saccharides, such as lactose, sucrose, anhydrous maltose, D-fructose, dextran (for example, Dextran 40), glucose, and the like; surfactants, such as polyoxyethylene hydrogenated castor oil [HCO: for example, Cremophor RH40 (BASF), HCO-40, HCO-60 (Nikko Chemicals)], polyoxyethylene polyoxypropylene glycol [for example, Pluronic F68 (Asahi Denka and the like)], polyoxyethylene sorbitan higher fatty acid esters [Tween: for example, Tween 80 (Kanto Chemical)], and the like; salts, such as sodium chloride, magnesium chloride, and the like; organic acids, such as citric acid, tartaric acid, and the like; amino acids, such as glycine, β-alanine, lysine hydrochloride, and the like; and aminosaccharides, such as meglumine and the like.

As another embodiment, PEG, PVP, D-mannitol, D-sorbitol, xylitol, lactose, sucrose, anhydrous maltose, D-fructose, dextran, glucose, polyoxyethylene polyoxypropylene glycol, sodium chloride, magnesium chloride, citric acid, tartaric acid, glycine, β-alanine, lysine hydrochloride, or meglumine may be used. As still another embodiment, PEG, PVP, D-mannitol, lactose, sucrose, sodium chloride, polyoxyethylene polyoxypropylene glycol, or the like may be used.

These hydrophilic bases may be used alone, or as an appropriate combination of two or more thereof.

The content of the hydrophilic base is not particularly limited, so long as it is an amount capable of controlling the release of the drug to the extent that the release of the drug is not affected by food. The content of the hydrophilic base is, for example, 5% by weight to 75% by weight, 5% by weight to 70% by weight in another embodiment, and 20% by weight to 60% by weight in still another embodiment.

The pharmaceutical composition for modified release of the present invention may be prepared as various dosage forms, which include, for example, formulations for oral administration such as tablets, capsules (including microcapsules), granules, and powder, and formulations for parenteral administration such as suppositories (for example, rectal suppositories or vaginal suppositories). These formulations may be safely administered orally or parenterally. Formulations for oral administration such as tablets, capsules, and granules may be selected in another embodiment.

The pharmaceutical composition for modified release of the present invention may be prepared by mixing the drug, the hydrogel-forming polymers, and the hydrophilic base, and forming the mixture into a predetermined shape. The mixing and forming may be carried out in accordance with conventional methods widely used in the technical field for formulation. A pharmaceutically acceptable carrier may be used in the mixing and/or forming, if desired.

In the preparation of the pharmaceutical composition for modified release of the present invention, further various pharmaceutical additives may be used, if desired. Such pharmaceutical additives are not particularly limited, so long as they are pharmaceutically acceptable. Examples of the pharmaceutical additives include various organic or inorganic carrier substances which are widely used as formulation materials, such as fillers, lubricants, binders, and disintegrating agents. Other formulation additives such as preservatives, antioxidants, stabilizers, film coating agents, coloring agents, and sweeteners may be used, if desired.

Examples of the fillers include lactose, sucrose, D-mannitol, D-sorbitol, starch, gelatinized starch, dextrin, crystalline cellulose, low substituted hydroxypropyl cellulose, carboxymethyl cellulose sodium, gum arabic, dextrin, pullulan, light anhydrous silicic acid, synthetic aluminum silicate, magnesium aluminate metasilicate, and the like.

Examples of the lubricants include magnesium stearate, calcium stearate, talc, colloidal silica, and the like.

Examples of the binders include gelatinized starch, sucrose, gelatin, gum arabic, methylcellulose, carboxymethyl cellulose, carboxymethyl cellulose sodium, crystalline cellulose, sucrose, D-mannitol, trehalose, dextrin, pullulan, hydroxypropyl cellulose, hydroxypropyl methylcellulose, polyvinylpyrrolidone, and the like.

Examples of the disintegrating agents include lactose, sucrose, starch, carboxymethyl cellulose, carboxymethyl cellulose calcium, croscarmellose sodium, carboxymethyl starch sodium, light anhydrous silicic acid, low substituted hydroxypropylcellulose, and the like.

Examples of the preservatives include p-hydroxybenzoate esters, chlorobutanol, benzyl alcohol, phenethyl alcohol, dehydroacetic acid, sorbic acid, and the like.

The antioxidants are not particularly limited, so long as it can avoid the effects of dissolution behavior. Examples of the antioxidants include butylated hydroxytoluene (BHT), propyl gallate (PG), butylhydroxyanisol (BHA), ascorbic acid, sodium ascorbate, erythorbic acid, sodium nitrite, sodium bisulfite, sodium pyrosulfite, citric acid, and edetate sodium; BHT, PG, and sodium ascorbate in another embodiment; and BHT in still another embodiment.

Examples of the stabilizers include yellow ferric oxide, red ferric oxide, black iron oxide, and the like.

Examples of the film coating agents include pharmaceutically commonly-used bases, such as water-soluble polymers, plasticizers, and inorganic substances, or a combination thereof.

Examples of the coloring agents include water-soluble edible tar pigments (examples: edible pigments such as food red No. 2, food red No. 3, food yellow No. 4, food yellow No. 5, food blue No. 1, and food blue No. 2), water-insoluble lake pigments (examples: aluminum salts of the above water-soluble edible tar pigments), natural pigments (examples: β-carotene, chlorophyll, and colcothar), and the like.

Examples of the sweeteners include saccharin sodium, dipotassium glycyrrhizinate, aspartame, stevia, and the like.

These carriers or formulation additives may be used alone, or as an appropriate combination of two or more thereof.

With respect to the contents thereof, they may be used in appropriate amounts. For example, the content of the antioxidant is 0.025% by weight to 0.25% by weight with respect to the total weight of the formulation, and that of the stabilizer is 0.05% by weight to 1% by weight with respect to the total weight of the formulation.

Hereinafter, the process of manufacturing the pharmaceutical composition for modified release of the present invention will be explained, the present invention is not limited to the following particular embodiments.

The pharmaceutical composition for modified release of the present invention may be prepared by known methods per se, such as dry granulation, wet granulation, fluidized bed granulation, intermittent granulation, agitation granulation, or the like.

As a method of de-lumping or pulverizing the drug, conventional crushing or pulverizing methods may be applied, for example, using an impact mill (Hosokawa Micron Corporation; Fine Impact Mill), a dry & wet mill (Powrex Corporation: Comil), or a cutting mill granulator (Dalton Corporation; Power Mill).

As a method of pulverizing the hydrophilic base, the hydrogel-forming polymer, or the formulation additives, conventional pulverizing methods may be applied, for example, using an impact mill (Hosokawa Micron Corporation; Fine Impact Mill or Sample Mill) or a jet mill (Horkos Corp; Jet Mill).

As a method of granulating the drug, conventional granulation methods may be used. Examples of such methods include a fluidized bed granulation method, an intermittent granulation method, an agitation granulation method, a high-speed agitation granulation method, a tumbling fluidized bed granulation method, an extrusion granulation method, a pulverization granulation method, a dry granulation method, and the like. In another embodiment, examples thereof include a fluidized bed granulation method, an intermittent granulation method, an agitation granulation method, a high-speed agitation granulation method, a tumbling fluidized bed granulation method, and a dry granulation method, and any method capable of granulating the drug may be used. Examples of a granulator include a fluidized bed granulator (for example, Flow Coater; Freund Corporation, or GPCG; Glatt GmbH), a granulation and coating apparatus equipped with a horizontal rotating disc having a flat powder contact portion [for example, a centrifugal fluidizing granulator (for example, CF granulator; Freund Corporation)], a granulation and coating apparatus having a rotating disk with a flat surface placed at the bottom of a fluidized bed and having an aeration portion (for example, Spiralflow, or Flowcoater with a rotor container; Freund Corporation), and a dry granulator in which material powder is directly compressed, molded, crushed, and sieved (for example, Roller Compactor; Freund Corporation).

In the dry granulation, for example, the drug, the hydrogel-forming polymer, the hydrophilic base, and additives such as a filler may be compression-molded using a dry granulator, and then, may be crushed and sieved to obtain granulated products having a desired size.

In the wet granulation, for example, while the drug, the hydrogel-forming polymer, the hydrophilic base, and additives such as a filler is fluidized, an appropriate amount of water or a liquid containing the hydrophilic base and the binder may be sprayed. The liquid containing the hydrophilic base may be prepared by dissolving or dispersing the essential component in a solvent such as water, ethanol, methanol, or the like. These solvents may be used as an appropriate mixture thereof.

The amount of water used in the granulation is not particularly limited, so long as the binder or formulation additives may be uniformly dissolved and/or suspended (dispersed) in the water. When the hydrophilic base is used in the solid form, the amount of water is not particularly limited, so long as the hydrogel-forming polymer can be granulated.

When the hydrophilic base is used in the liquid form, the amount of water to the hydrogel-forming polymer is generally 10% by weight or less, 8% by weight or less in another embodiment, and 5% by weight or less in still another embodiment. A method of adding water in the granulation is not particularly limited, so long as a nonuniform mixture consisting of untreated powder and aggregates, which are generally powdery, is not generated. Examples thereof include a continuous spray method in which water is continuously added, an intermittent spray method in which a dry step (and a shaking step, if desired) is carried out during the granulation step, and the like.

The addition rate of water in the granulation is not particularly limited, so long as a nonuniform mixture consisting of untreated powder and aggregates, which are generally powdery, is not generated. In the fluidized bed granulation, the addition rate of water to the hydrogel-forming polymer is generally 0.1% by weight/min. to 1% by weight/min., 0.2% by weight/min. to 0.8% by weight/min. in another embodiment, and 0.4% by weight/min. to 0.6% by weight/min. in still another embodiment.

The temperature of the powder in the granulation is not particularly limited, so long as it does not induce thermal denaturation of the hydrogel-forming polymer. The temperature is, for example, 20° C. to the melting point (62° C. to 67° C.) of the hydrogel-forming polymer, 20° C. to 50° C. in another embodiment, 20° C. to 35° C. in still another embodiment, and 25° C. to 30° C. in still another embodiment.

The concentration of the binder liquid as a solid content which may be used in the granulation is, for example, 1% to 20% as a formulation amount. The binder is not particularly limited, so long as it is pharmaceutically acceptable.

The binder may be added in the solid form to a granulator, and then, water may be sprayed as the binder liquid. Alternatively, the binder may be dissolved in water, and then, the resulting binder liquid may be sprayed.

An appropriate spray rate of the binder liquid varies according to a production method to be applied or its production scale. In a 1-kg scale production by the fluidized bed granulation, the spray rate is 2 g/min. to 20 g/min., and 5 g/min. to 15 g/min. in another embodiment.

An appropriate temperature of the product in the granulation is 15° C. to 50° C., and 15° C. to 40° C. in another embodiment.

The resulting granulated products may be, for example, dried or heated.

In the drying step, an apparatus and a method are not particularly limited, so long as the granulated products can be dried. Examples of an apparatus for drying include a fluidized bed granulator (for example, Flow Coater; Freund Corporation, or GPCG; Glatt GmbH), a granulation and coating apparatus equipped with a horizontal rotating disc having a flat powder contact portion [for example, a centrifugal fluidizing granulator (for example, CF granulator; Freund Corporation)], a granulation and coating apparatus having a rotating disk with a flat surface placed at the bottom of a fluidized bed and having an aeration portion (for example, Spiralflow, or Flowcoater with a rotor container; Freund Corporation), and the like. The conditions for drying are not particularly limited, so long as the granulated products may be generally dried in the fluidized bed. The drying of the granulated products will be almost completed, for example, under the conditions in which the dry inlet air temperature is 50° C. and the drying is carried out until the temperature of the granulated products becomes 40° C. and, in another embodiment, under the conditions in which the dry inlet air temperature is 40° C. and the drying is carried out until the temperature of the granulated products becomes 30° C. As the drying method, forced-air drying or drying under reduced pressure may be used.

After the completion of the granulation, an anti-oxidant may be added.

The granulated products may be sieved.

In the sieving step, an apparatus and a method are not particularly limited, so long as the granulated products can be sieved. Examples of an apparatus for sieving include a screen, a dry & wet mill (Powrex Corporation: Comil), a cutting mill granulator (Dalton Corporation; Power Mill), and the like. The conditions for sieving are not particularly limited, so long as the granulated products may be generally sieved to obtain particles having a desired size.

After the completion of the sieving, an anti-oxidant may be added.

Examples of tabletting include a direct tabletting method in which the drug, the hydrophilic base, and the hydrogel-forming polymer are mixed with an appropriate additive(s), and the mixture is compression-molded to obtain tablets; a method in which a composition obtained by a wet granulation (the granulation is carried out by spraying a mixture of the drug, the hydrophilic base, the hydrogel-forming polymer, and additives with a binder liquid) or a melting granulation (the granulation is carried out by heating a mixture of the drug, the hydrophilic base, the hydrogel-forming polymer, and an appropriate low-melting substance) is formed into tablets; and the like.

A rotary tabletting machine, a single punch tabletting machine, and the like may be used as a tabletting machine. A method as well as an apparatus is not particularly limited, so long as a compression-molded product (preferably tablets) can be pharmaceutically produced.

After the tabletting, the obtained tablets may be dried. The initial water content of the tablet is, for example, 2% by weight/tablet or less, 1.5% by weight/tablet or less in another embodiment, and 0.9% by weight/tablet or less in still another embodiment.

After the tabletting, the obtained tablets may be film coated using a pan coating machine at an amount of 1% by weight to 5% by weight per tablet.

EXAMPLES

The present invention will now be further illustrated by, but is by no means limited to, the following Examples.

Example 1

In a mortar, 10 g of compound A, 2.5 g of polyethylene oxide (Dow chemical; product name: WSR N-60K; The same compound was used in the following Examples, unless otherwise specified.), and 7.5 g of polyethylene glycol (Sanyo Chemical Industries, Ltd.; PEG 6000; The same compound was used in the following Examples.) were mixed well. The mixture was formed into tablets using Autograph (Shimadzu; The same apparatus was used in the following Examples.) to obtain a pharmaceutical composition for modified release of the present invention having a tablet weight of 400 mg.

Example 2

In a mortar, 10 g of compound A, 3.5 g of polyethylene oxide, and 6.5 g of polyethylene glycol were mixed well, and the mixture was formed into tablets using Autograph to obtain a pharmaceutical composition for modified release of the present invention having a tablet weight of 400 mg.

Example 3

In a mortar, 10 g of compound A, 6.25 g of polyethylene oxide, and 5 g of polyethylene glycol were mixed well, and the mixture was formed into tablets using Autograph to obtain a pharmaceutical composition for modified release of the present invention having a tablet weight of 425 mg.

Example 4

In a mortar, 10 g of compound A, 5 g of hydroxypropyl methylcellulose (Shin-Etsu Chemical Co., Ltd.; HPMC90SH-4000SR), and 5 g of polyethylene glycol were mixed well, and the mixture was formed into tablets using Autograph to obtain a pharmaceutical composition for modified release of the present invention having a tablet weight of 400 mg.

Example 5

In a mortar, 10 g of compound A, 5 g of hydroxypropyl methylcellulose (Shin-Etsu Chemical Co., Ltd.; HPMC90SH-100000SR), and 5 g of polyethylene glycol were mixed well, and the mixture was formed into tablets using Autograph to obtain a pharmaceutical composition for modified release of the present invention having a tablet weight of 400 mg.

Example 6

In a mortar, 10 g of compound A, 7.5 g of hydroxypropyl methylcellulose (Shin-Etsu Chemical Co., Ltd.; HPMC90SH-100SR), and 2.5 g of polyethylene glycol were mixed well, and the mixture was formed into tablets using Autograph to obtain a pharmaceutical composition for modified release of the present invention having a tablet weight of 400 mg.

Example 7

After 400 g of compound A, 140 g of polyethylene oxide, 251.2 g of polyethylene glycol, 0.8 g of finely ground BHT (Merck; The same compound was used in the following Examples.) and 8 g of magnesium stearate were weighed out, these compounds were mixed using a mixer. The mixture was compression-molded using Roller Compactor Mini (Freund Corporation) and sieved to obtain a pharmaceutical composition for modified release (granules) of the present invention. The obtained granules were formed into tablets using a rotary tabletting machine (Hata Iron Works Co., Ltd.; The same apparatus was used in the following Examples.) to obtain a pharmaceutical composition for modified release (tablets) of the present invention having a tablet weight of 400 mg.

Example 8

The tablets obtained in Example 7 were coated with a film coating agent [Colorcon; Opadry (containing yellow ferric oxide as a stabilizer); The same agent was used in the following Examples, unless otherwise specified.] dispersed into water to obtain a pharmaceutical composition for modified release (tablets) of the present invention.

Example 9

Into a fluidized bed granulating apparatus GPCG-5 (Freund Corporation; The same apparatus was used in the following Examples.), 1500 g of de-lumped compound A, 1050 g of polyethylene oxide, and 1764 g of polyethylene glycol were loaded, and granulated with 1350 g of a 10% by weight aqueous solution of hydroxypropyl cellulose (Nippon Soda Co., Ltd.; HPC-SL; The same compound was used in the following Examples.) to obtain a pharmaceutical composition for modified release (granules) of the present invention. The resulting pharmaceutical composition for modified release (granules) of the present invention was sieved and mixed with 4 g of finely ground BHT and 30 g of magnesium stearate, and the mixture was formed into tablets using a rotary tabletting machine to obtain a pharmaceutical composition for modified release (tablets) of the present invention having a tablet weight of 300 mg. The obtained tablets were spray-coated with an aqueous dispersion of the film coating agent using HiCoater to obtain a pharmaceutical composition for modified release (tablets) of the present invention having a tablet weight of 309 mg.

Example 10

Into a fluidized bed granulating apparatus GPCG-5, 1500 g of de-lumped compound A, 1050 g of polyethylene oxide, 1764 g of polyethylene glycol, and 135 g of hydroxypropyl cellulose (HPC-SL) were loaded, and granulated with purified water to obtain a pharmaceutical composition for modified release (granules) of the present invention. The resulting pharmaceutical composition for modified release (granules) of the present invention was sieved and mixed with 4 g of finely ground BHT and 30 g of magnesium stearate, and the mixture was formed into tablets using a rotary tabletting machine to obtain a pharmaceutical composition for modified release (tablets) of the present invention having a tablet weight of 300 mg. The obtained tablets were spray-coated with an aqueous dispersion of the film coating agent using HiCoater to obtain a pharmaceutical composition for modified release (tablets) of the present invention having a tablet weight of 309 mg.

Example 11

After 400 g of compound A, 100 g of polyethylene oxide, 290 g of polyethylene glycol, 2 g of finely ground BHT, and 8 g of magnesium stearate were weighed out, these compounds were mixed using a mixer. The mixture was compression-molded using Roller Compactor Mini and sieved to obtain a pharmaceutical composition for modified release (granules) of the present invention. The obtained granules were formed into tablets using a rotary tabletting machine to obtain a pharmaceutical composition for modified release (tablets) of the present invention having a tablet weight of 400 mg.

Example 12

In a mortar, 10 g of compound A, 2.5 g of polyethylene oxide (Dow chemical; product name: WSR Coagulant), and 12.5 g of polyethylene glycol were mixed well. The mixture was formed into tablets using Autograph to obtain a pharmaceutical composition for modified release of the present invention having a tablet weight of 400 mg.

Example 13

In a mortar, 10 g of compound A, 0.5 g of polyethylene oxide (Dow chemical; product name: WSR 301), and 5 g of polyethylene glycol were mixed well. The mixture was formed into tablets using Autograph to obtain a pharmaceutical composition for modified release of the present invention having a tablet weight of 310 mg.

Example 14

In a mortar, 5 g of compound A, 15 g of polyethylene oxide, and 5 g of polyethylene glycol were mixed well. The mixture was formed into tablets using Autograph to obtain a pharmaceutical composition for modified release of the present invention having a tablet weight of 250 mg.

Example 15

In a mortar, 10 g of compound A, 10 g of polyethylene oxide (Dow chemical; product name: WSR N-12K), and 5 g of D-mannitol (Towa Chemical Industry Co., Ltd; product name: Mannit P) were mixed well. The mixture was formed into tablets using Autograph to obtain a pharmaceutical composition for modified release of the present invention having a tablet weight of 500 mg.

Example 16

In a mortar, 2 g of compound A, 2 g of polyethylene oxide, and 10 g of polyethylene glycol were mixed well. The mixture was formed into tablets using Autograph to obtain a pharmaceutical composition for modified release of the present invention having a tablet weight of 350 mg.

Example 17

Into a fluidized bed granulating apparatus GPCG-5, 400 g of de-lumped compound A, 1120 g of polyethylene oxide, and 2313.6 g of polyethylene glycol were loaded, and granulated with 1200 g of a 10% by weight aqueous solution of hydroxypropyl cellulose to obtain a pharmaceutical composition for modified release (granules) of the present invention. The resulting pharmaceutical composition for modified release (granules) of the present invention was sieved and mixed with 6.4 g of finely ground BHT and 40 g of magnesium stearate, and the mixture was formed into tablets using a rotary tabletting machine to obtain a pharmaceutical composition for modified release (tablets) of the present invention having a tablet weight of 250 mg. The obtained tablets were spray-coated with an aqueous dispersion of the film coating agent (containing yellow ferric oxide and red ferric oxide as stabilizers) using HiCoater to obtain a pharmaceutical composition for modified release (tablets) of the present invention having a tablet weight of 257.5 mg.

The formulations in Examples 1 to 17 are shown in Tables 1 to 3.

TABLE 1

| Examples | 1 | 2 | 3 | 4 | 5 | 6 |
|---|---|---|---|---|---|---|
| compound A (g) | 10 | 10 | 10 | 10 | 10 | 10 |
| PEO WSR N-60K (g) | 2.5 | 3.5 | 6.25 | — | — | — |
| HPMC 90SH-4000SR (g) | — | — | — | 5 | — | — |
| HPMC 90SH-100000SR (g) | — | — | — | — | 5 | — |
| HPMC 90SH-100SR (g) | — | — | — | — | — | 7.5 |
| PEG (g) | 7.5 | 6.5 | 5 | 5 | 5 | 2.5 |

TABLE 2

| Examples | 7 | 8 | 9 | 10 | 11 |
|---|---|---|---|---|---|
| compound A (g) | 400 | 400 | 1500 | 1500 | 400 |
| PEO WSR N-60K (g) | 140 | 140 | 1050 | 1050 | 100 |
| PEG (g) | 251.2 | 251.2 | 1764 | 1764 | 290 |
| HPC-SL (g) | — | — | 135 | 135 | — |
| magnesium stearate (g) | 8 | 8 | 30 | 30 | 8 |
| BHT (g) | 0.8 | 0.8 | 4 | 4 | 2 |
| film coating agent (g) | — | 23.7 | 134 | 134 | — |

TABLE 3

| Examples | 12 | 13 | 14 | 15 | 16 | 17 |
|---|---|---|---|---|---|---|
| compound A (g) | 10 | 10 | 5 | 10 | 2 | 400 |
| PEO WSR N-60K (g) | — | — | 15 | — | 2 | 1120 |
| PEO WSR coagulant (g) | 2.5 | — | — | — | — | — |
| PEO WSR 301 (g) | — | 0.5 | — | — | — | — |
| PEO WSR N-12K (g) | — | — | — | 10 | — | — |
| PEG (g) | 12.5 | 5 | 5 | — | 10 | 2313.6 |
| D-mannitol | — | — | — | 5 | — | — |
| HPC-SL (g) | — | — | — | — | — | 120 |
| magnesium stearate (g) | — | — | — | — | — | 40 |
| BHT (g) | — | — | — | — | — | 6.4 |
| film coating agent (g) | — | — | — | — | — | 120 |

Comparative Example 1

After 400 g of pulverized compound A was mixed with 1200 g of D-mannitol, 320 g of purified water was further added, and the whole was kneaded using an agitation granulator (Powrex Corporation; VG-25). The resulting aggregate was sieved through a screen having an opening of 850 μm, and dried using a fluidized bed granulating apparatus (Freund Corporation; FLO-1). The dried products were sieved through a screen having an opening of 500 μm, and filled into No. 1 capsules at a content of 320 mg per capsule to obtain a pharmaceutical composition for comparison containing 80 mg of compound A.

EXPERIMENTAL EXAMPLES

1. Dissolution test

The pharmaceutical compositions prepared in Examples 2, 8, and 9 were subjected to a dissolution test carried out in accordance with a USP dissolution test (paddle method). As a test fluid, 900 mL of a phosphate buffer (pH 6.8) was used. The pharmaceutical composition prepared in Comparative Example 1 was tested in accordance with a dissolution test, method 2 described in the Japanese Pharmacopoeia. As a test fluid, 900 mL of a Mc. Ilvain buffer (pH 6.8) was used, and the paddle rotation speed was 50 rpm.

The results are shown in Table 4. The dissolution rate after 1.5 hours of the pharmaceutical composition for modified release prepared in each Example was less than 40%. By contrast, the composition prepared in Comparative Example showed a high dissolution rate of 85% or more after 0.5 hour.

TABLE 4

|  | Example 2 | Example 8 | Example 9 | Comparative Example 1 |
|---|---|---|---|---|
| 0.5 hr. | — | — | — | 95% |
| 1.5 hr. | 35% | 39% | 32% | — |
| 2.5 hr. | 57% | 61% | 54% | — |
| 4.5 hr. | 93% | 95% | 92% | — |

2. Stability Test

Plastic bottles were filled with the pharmaceutical composition for modified release prepared in Example 11, and sealed. These bottles were preserved under the conditions at 40° C. and 75% RH or at 60° C. for 3 months. After the preservation, each pharmaceutical composition was subjected to a dissolution test carried out in accordance with a USP dissolution test (paddle method). As a test fluid, 900 mL of a phosphate buffer (pH 6.8) was used. The results are shown in FIG. 1. The acceleration of a dissolution rate was not observed after the preservation for 3 months under the conditions at 40° C. and 75% RH or at 60° C., and the results were indicative that the pharmaceutical composition was stable.

The pharmaceutical compositions for modified release prepared in Examples 8 and 9 were packed with alminum/alminum blister, and preserved under the conditions at 40° C. and 75% RH for 6 months. After the preservation, each pharmaceutical composition was subjected to a dissolution test carried out in accordance with a USP dissolution test (paddle method). As a test fluid, 900 mL of a phosphate buffer (pH 6.8) was used. As a result, changes in the dissolution rate at the point showing a dissolution rate of approximately 50% were 2% and 3%, with respect to the pharmaceutical compositions prepared in Examples 8 and 9, respectively, and the results were indicative that the pharmaceutical compositions were stable.

The pharmaceutical composition for modified release prepared in Example 17 was exposed to 1.2 million Lux·hr of light. After the exposure, the pharmaceutical composition was subjected to a dissolution test carried out in accordance with a USP dissolution test (paddle method). As a test fluid, 900 mL of a phosphate buffer (pH 6.8) was used. As a result, the change in the dissolution rate at the point showing a dissolution rate of approximately 50% was less than 1%, and the result was indicative that the pharmaceutical composition was stable.

3. Pharmacokinetics (PK) Test in Human

The pharmaceutical composition for modified release prepared in Example 8, which contained the equivalent corresponding to 200 mg of compound A, was administered to healthy persons in a fasted state or after 30 minutes from the intake of food, and the plasma levels of the drug were measured.

For comparison, 2 capsules of the pharmaceutical composition (conventional formulation) prepared in Comparative Example 1, which contained the equivalent corresponding to 160 mg of compound A, was administered to healthy persons in a fasted state or after 30 minutes from the intake of food, and the plasma levels of the drug were measured.

With respect to the conventional formulation, the rate of decrease of Cmax in the fed state was 67%, in comparison with that in a fasted state, and the rate of decrease of AUC was 47% (Cmax in the fasted state was approximately three times higher than that in the fed state). With respect to the pharmaceutical composition for modified release of the present invention, the rate of decrease of Cmax in free-feeding was 42%, in comparison with that in a fasted state, and the rate of decrease of AUC was 25%. These results indicated that the reductions of Cmax and AUC caused by food intake could be significantly alleviated by the pharmaceutical composition for modified release of the present invention.

INDUSTRIAL APPLICABILITY

According to the present invention, a pharmaceutical composition for modified release in which the changes in AUC and Cmax caused by food intake can be decreased by controlling a releasing rate of the active ingredient can be provided.

As above, the present invention was explained with reference to particular embodiments, but modifications and improvements obvious to those skilled in the art are included in the scope of the present invention.

The invention claimed is:

1. A pharmaceutical composition, comprising 10 mg to 200 mg of (R)-2-(2-aminothiazol-4-yl)-4'-[2-[(2-hydroxy-2-phenylethyl)amino]ethyl]acetic acid anilide, or a pharmaceutically acceptable salt thereof, in a sustained release hydrogel-forming formulation comprising a hydrogel-forming polymer having an average molecular weight of 100,000 to 8,000,000 and an additive having a water solubility of at least 0.1 g/mL at 20±5° C.,
    wherein the hydrogel-forming polymer is at least one compound selected from the group consisting of polyethylene oxide, hydroxypropyl methylcellulose, hydroxypropyl cellulose, carboxymethyl cellulose sodium, hydroxyethyl cellulose, and a carboxyvinyl polymer,
    wherein the additive is at least one selected from the group consisting of polyethylene glycol, polyvinylpyrrolidone, D-mannitol, D-sorbitol, xylitol, lactose, sucrose, anhydrous maltose, D-fructose, dextran, glucose, polyoxyethylene hydrogenated castor oil, polyoxyethylene polyoxypropylene glycol, polyoxyethylene sorbitan higher fatty acid ester, sodium chloride, magnesium chloride, citric acid, tartaric acid, glycine, (3-alanine, lysine hydrochloride, and meglumine, and
    wherein a drug dissolution rate from the pharmaceutical composition is 39% or less after 1.5 hours, and at least 75% after 7 hours, as measured in accordance with United States Pharmacopoeia in 900 mL of a USP buffer having a pH of 6.8 at a paddle rotation speed of 200 rpm.

2. The pharmaceutical composition according to claim 1, wherein the additive is at least one selected from the group consisting of polyethylene glycol, polyvinylpyrrolidone, D-mannitol, lactose, sucrose, sodium chloride, and polyoxyethylene polyoxypropylene glycol.

3. The pharmaceutical composition according to claim 1, wherein an amount of the additive is 5% by weight to 75% by weight with respect to a total weight of the pharmaceutical composition.

4. The pharmaceutical composition according to claim 3, wherein the amount of the additive is 5% by weight to 70% by weight with respect to the total weight of the pharmaceutical composition.

5. The pharmaceutical composition according to claim claim 1, wherein the hydrogel-forming polymer is at least one compound selected from the group consisting of polyethylene oxide, hydroxypropyl methylcellulose, and hydroxypropyl cellulose.

6. The pharmaceutical composition according to claim 1, further comprising an antioxidant.

7. The pharmaceutical composition according to claim 6, wherein the antioxidant is at least one compound selected from the group consisting of butyl hydroxytoluene, propyl gallate, and sodium ascorbate.

8. The pharmaceutical composition according to claim 7, wherein the antioxidant is butyl hydroxytoluene.

9. The pharmaceutical composition according to claim 6, wherein an amount of the antioxidant is 0.025% by weight to 0.25% by weight with respect to a total weight of the pharmaceutical composition.

10. The pharmaceutical composition according to claim 1, further comprising a stabilizer.

11. The pharmaceutical composition according to claim 10, wherein the stabilizer is at least one compound selected from the group consisting of yellow ferric oxide, red ferric oxide, and black iron oxide.

12. The pharmaceutical composition according to claim 11, wherein the stabilizer is yellow ferric oxide and/or red ferric oxide.

13. The pharmaceutical composition according to claim 10, wherein an amount of the stabilizer is 0.05% by weight to 1% by weight with respect to a total weight of the pharmaceutical composition.

14. The pharmaceutical composition according to claim 1, wherein the drug dissolution rate from the pharmaceutical composition is at least 92% after 4.5 hours.

15. The pharmaceutical composition according to claim 1, wherein the average molecular weight of the hydrogel-forming polymer is 100,000 to 2,000,000.

16. The pharmaceutical composition according to claim 1, comprising 10 mg to 200 mg of (R)-2-(2-aminothiazol-4-yl)-4'-[2-[(2-hydroxy-2-phenylethyl)amino]ethyl]acetic acid anilide.

17. A tablet, comprising the pharmaceutical composition according to claim 1.

18. A tablet, comprising the pharmaceutical composition according to claim 16.

19. A method for treating overactive bladder comprising administering the tablet according to claim 17 to a subject in need thereof.

20. A method for treating overactive bladder comprising administering the tablet according to claim 18 to a subject in need thereof.

21. The pharmaceutical composition according to claim 1, wherein the average molecular weight of the hydrogel-forming polymer is 100,000 to 5,000,000.

22. A pharmaceutical composition, comprising 10 mg to 200 mg of (R)-2-(2-aminothiazol-4-yl)-4'-[2-[(2-hydroxy-2-phenylethyl)amino]ethyl]acetic acid anilide, or a pharmaceutically acceptable salt thereof, in a sustained release hydrogel-forming formulation comprising a means for forming a hydrogel and a means for ensuring penetration of water into the pharmaceutical composition, wherein a drug dissolution rate from the pharmaceutical composition is 39% or less after 1.5 hours, and at least 75% after 7 hours, as measured in accordance with United States Pharmacopoeia in 900 mL of a USP buffer having a pH of 6.8 at a paddle rotation speed of 200 rpm.

23. The pharmaceutical composition according to claim 22, comprising 10 mg to 200 mg of (R)-2-(2-aminothiazol-4-yl)-4'-[2-[(2-hydroxy-2-phenylethyl)amino]ethyl]acetic acid anilide.

24. A tablet, comprising the pharmaceutical composition according to claim 22.

25. A tablet, comprising the pharmaceutical composition according to claim 23.

* * * * *

UNITED STATES PATENT AND TRADEMARK OFFICE
CERTIFICATE OF CORRECTION

Page 1 of 2

PATENT NO. : 10,842,780 B2
APPLICATION NO. : 15/432854
DATED : November 24, 2020
INVENTOR(S) : Yuuki Takaishi et al.

It is certified that error appears in the above-identified patent and that said Letters Patent is hereby corrected as shown below:

On the Title Page

Item [56] REFERENCES CITED:

Page 2
Column 1:
Line 4, Foreign References "JP 2008-532953 8/2006" should read --JP 2008-532953 8/2008--;
Line 26, Other Publications "tion Report, 4 pages (English translation)." should read --tion Report, received Feb. 4, 2014, 4 pages (English translation).--;
Line 30, "Japanese Patent Application No. 2010-531838, first Office Action, dated Dec. 28, 2010, 4 pages (English translation)." should read --Japanese Patent Application No. 2010-531838, second Office Action, dated Dec. 28, 2010, 4 pages (English translation).--;
Column 2:
Line 17, "dated Aug. 1, 2018," should read --mailed Aug. 1, 2018,--;
Line 70, "Humans" should read --Humans:--;

Page 3
Column 2:
Lines 9-10, "Wolfers Klower" should read --Wolters Kluwer--;

Page 4
Column 1:
Line 21, "Nov. 2015)." should read --Nov. 9, 2015).--;
Column 2:
Line 22, "Stephen Bym et al.," should read --Stephen Byrn et al.,--; and
Line 64, "World J. Ural." should read --World J. Urol.--.

Signed and Sealed this
Thirteenth Day of July, 2021

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 10,842,780 B2

In the Specification

Column 2:
Line 54, "a clinical trial in human" should read --a human clinical trial--; and
Line 64, "profiles is" should read --profiles are--.

Column 5:
Line 52, "Mc. Ilvain buffer," should read --McIlvaine buffer,--.

Column 6:
Line 13, "$Rd(AUC)=[AUC(FS)-AUC(FI)]1\times 100/AUC(FS)$" should read --$Rd(AUC)=[AUC(FS)-AUC(FI)]\times 100/AUC(FS)$--.

Column 7:
Line 41, "extend" should read --extent--.

Column 10:
Line 3, "in case" should read --in the case--.

Column 12:
Line 57, "is fluidized," should read --are fluidized,--.

Column 18:
Line 60, "Mc. Ilvain buffer" should read --McIlvaine buffer--.

Column 19:
Line 25, "alminum/" should read --aluminum/--; and
Line 26, "alminum blister," should read --aluminum blister,--.

In the Claims

Column 20:
Line 41, "(3-alanine," should read --β-alanine,--; and
Line 61, "claim" should be deleted.